United States Patent [19]
Oksman et al.

[11] Patent Number: 5,120,321
[45] Date of Patent: Jun. 9, 1992

[54] SAFETY DISPOSABLE NEEDLE

[76] Inventors: Henry C. Oksman, 20 Wagon Wheel Rd., Mamaroneck, N.Y. 10543; Joseph Eisner, 219 E. 32nd St., New York, N.Y. 10016

[21] Appl. No.: 540,139

[22] Filed: Jun. 19, 1990

[51] Int. Cl.⁵ ............................................. A61M 5/32
[52] U.S. Cl. .................................... 604/198; 604/263
[58] Field of Search ............... 604/192, 197, 198, 263

[56] References Cited

U.S. PATENT DOCUMENTS

| | | | |
|---|---|---|---|
| 3,468,309 | 9/1969 | Drewe | 604/263 |
| 4,392,859 | 7/1983 | Dent | 604/263 |
| 4,755,170 | 7/1988 | Golden | 604/192 |
| 4,804,371 | 2/1989 | Vaillancourt | 604/263 |
| 4,846,809 | 7/1989 | Sims | 604/263 |
| 4,929,241 | 5/1990 | Kulli | 604/192 |
| 4,955,866 | 9/1990 | Corey | 604/192 |

FOREIGN PATENT DOCUMENTS

| | | | |
|---|---|---|---|
| 2209470 | 5/1989 | United Kingdom | 604/192 |
| 8900865 | 2/1989 | World Int. Prop. O. | 604/192 |

*Primary Examiner*—C. Fred Rosenbaum
*Assistant Examiner*—Sharon Finkel
*Attorney, Agent, or Firm*—Howard F. Mandelbaum

[57] ABSTRACT

A safety disposable needle has a shroud with a canted bore region slidably mounted thereon. A face of the shroud directed to engage the skin has an adhesive coating for fixing the shroud to the skin as the needle is withdrawn and its tip enters the shroud after which the shroud is separated from the skin as it engages an enlargement on the needle and is then canted to entrap the needle tip.

9 Claims, 1 Drawing Sheet 5,120,321

SAFETY DISPOSABLE NEEDLE

BACKGROUND OF THE INVENTION

Although exposed used syringe and intravenous needles have always presented a danger of transmitting infectious disease, the recent and highly publicized alarming spread of AIDS virus has focused attention on the problem. Whereas the possibility of an accidental engagement with the end of a used syringe or intravenous needle may have once been considered a minor annoyance associated with a pin prick, physicians, nurses, and other hospital and medical office personnel are now aware that their very lives are threatened by the existence of used syringe and intravenous needles which have not been properly discarded. In the course of a lawsuit recently given high notoriety, it was alleged that a physician contracted AIDS by accidentally pricking herself with a needle carelessly left among the bed sheets of an infected patient who had been injected with the needle.

The need for making a needle safe after use is well known but none of the solutions proposed to date adequately addresses the problem. In order to be effective, such a solution must be economical, that is, it must not unduly increase the cost of a syringe or intravenous needle assembly which is a high volume disposable item. Protection of the used needle must also be automatic so as to avoid compromise of safety by human error.

Proposed devices of the prior art fail to meet the foregoing criteria. For example, U.S. Pat. No. 4,790,828 to Dombrowski et al. for a Self-Capping Needle Assembly discloses a syringe with a relatively complex cap member having moving parts and projections that must be squeezed together to move the protective part of the cap member over the tip of the needle. U.S. Pat. No. 4,861,338 to Mathiesen et al. for a Safety Syringe is directed to a device for retracting the syringe needle into a sheath much like the writing cartridge of a ball point pen is retracted into the barrel of the pen. The foregoing devices of the prior art are relatively expensive and complex and their designs require the intervention of the physician, nurse or technician using the syringe or intravenous device to make the used needle safe.

SUMMARY OF THE INVENTION

The present invention overcomes the aforementioned disadvantages of the prior art by providing an apparatus and method for protecting against the tip of a used syringe or intravenous needle which is cost effective and requires no user intervention.

More specifically, the instant invention provides an apparatus and method for passing a fluid through the skin of a living being from a reservoir for storing or receiving the fluid, a hollow tubular needle with a reservoir end mounted on one end of the reservoir and an opposite penetrating end for penetrating the skin, a shroud axially slidably mounted on the needle for movement between a first position at which the penetrating end of the needle is exposed and a second position at which the penetrating end of the needle is covered by the shroud, the shroud having a hollow bore through which the needle completely extends when the shroud is in the first position, and an adhesive on its surface for releasably affixing the shroud to the skin, and the needle having an enlargement intermediate its ends larger than a narrowed region of the bore in the shroud for preventing the shroud from sliding entirely off the needle, whereby the shroud, when in the first position, exposes the penetrating end of the needle and engages the skin at the adhesive surface when the needle is inserted therein, and the shroud adheres to the skin while the needle is withdrawn therefrom for causing the shroud to slide over the penetrating end of the needle whereat the needle enlargement is engaged in the narrowed bore region of the shroud in the second position thereby causing the shroud to separate from the skin as withdrawal of the needle continues.

It is therefore an object of the invention to provide an apparatus and method for covering the tip of a syringe or intravenous needle after use.

Another object of the invention is to provide an apparatus and method for automatically covering the tip of a syringe or intravenous needle after use.

Still another object of the invention is to provide an apparatus and method for covering the tip of a syringe or intravenous needle after use by a device which can be employed at minimal cost.

Still a further object of the invention is to provide an apparatus and method for covering the tip of a syringe or intravenous needle after use which is reliable and cannot be readily undone.

Other and further objects of the invention will be apparent from the following drawings and description of a preferred embodiment of the invention in which like reference numerals are used to indicate like parts in the various views.

DESCRIPTION OF THE PREFERRED EMBODIMENT

Figure 1:
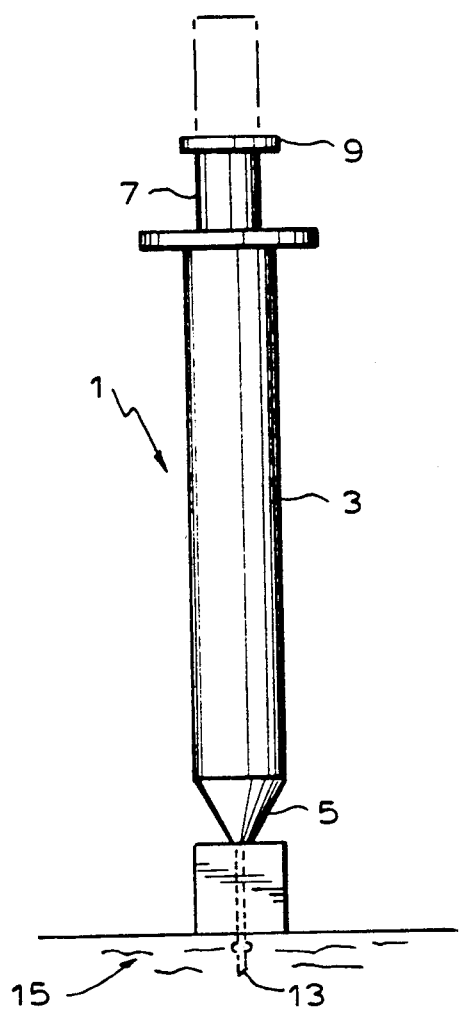
FIG. 1 is an elevation view of the apparatus of the preferred embodiment of the invention in an initial disposition.

Referring now to the drawings, there is shown a syringe 1 having an elongated hollow cylindrical reservoir 3 terminating at one end in a frustoconical portion 5. Slidably disposed in the reservoir 3 is a cylindrical plunger 7 with an enlarged thumb button 9 for pressing the plunger into the reservoir 7 to increase pressure on a fluid in the form of medication stored therein for injection, or for pulling the plunger out of the reservoir body to decrease pressure in the reservoir for filling the reservoir with a fluid, e.g., a medication stored in a bottle or blood or other body fluid drawn from a patient. The syringe reservoir 3 and plunger 7 are conventional.

Figure 2:
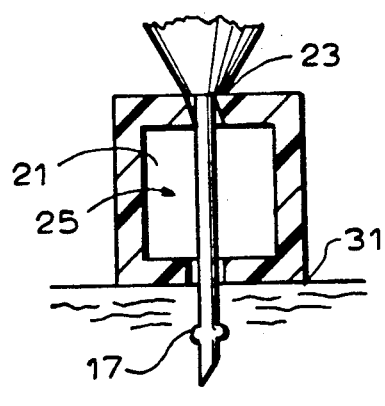
FIG. 2 is a fragmentary enlarged elevation view of the apparatus of the preferred embodiment of the invention in the disposition of FIG. 1.

Affixed to the frustoconical end of the syringe reservoir 7 is a hollow tubular needle 11 having a tip 13 capable of penetrating the skin of a living body. Intermediate the end of the needle 13 attached to the frustoconical end 5 of the syringe reservoir 3 and the tip 13 of the needle 11 is a limiter for preventing movement of the shroud 19 completely over the tip 13 and off the needle 11, in the form of an enlargement 17. The enlargement 17 should typically have an outer diameter on the order of ten to twenty per cent (10%-20%) of the outer diameter of needle 11 if the enlargement 17 is to be on a portion of the needle that enters the skin as shown in FIGS. 1 and 2. The enlargement 17 is shown in exaggerated size in the drawings for visibility. The enlargement 17 can be formed in a number of ways, e.g., by bulging the needle 11, by bending or crimping the needle 11, or by affixing a narrow circumferential band to the exterior of the needle 11.

Figure 4:
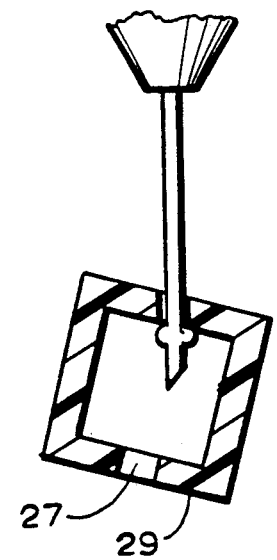
FIG. 4 is a fragmentary enlarged elevation view of the apparatus of the preferred embodiment of the invention in a final disposition.

Slidably disposed on the needle 11, as best seen in FIGS. 2 and 4, is a shroud in the form of a hollow cylindrical plug 19 having a substantially cylindrical stepped bore 21. The plug 19 need not be cylindrical but can have numerous other shapes including, without limitation, conical, C-shaped, spherical, rectangular, pyramidal, or almost any other shape which will have a surface able to adhere to the skin as will be more fully explained below. The plug 19 is preferably formed from a light weight semi-rigid elastomeric plastic or rubber material. At the end of the shroud 19 proximate the frustoconical end 5 of the syringe reservoir 3 the bore has a region 23 that is so narrow as to slidably frictionally engage the exterior of the needle 11, and preferably canted slightly, as shown in FIGS. 2 and 4, to aid friction and to help entrap the needle tip 13 within the bore 21 after the needle is used as will be more fully explained below.

Other means may be employed to apply friction to the needle as the plug 19 is slid along its length. For example, a resilient ball, or a spring, or a ball and spring may be partially recessed within a wall of the plug 19 in or adjacent the bore region 23.

The canted narrow bore region 23 leads into an enlarged bore region 25 which is desirably several times greater than the thickness of the needle 11. Finally the enlarged bore region 25 terminates in a narrow region 27 which frictionally slidably engages the exterior of the needle 11 when the needle 11 is disposed in the narrow bore region 27. Friction between the needle 11 and the inner wall of the shroud 19 takes place in the bore regions 23 and 27 and is enhanced by the canting of the bore region 23 in engagement with the needle 11. The bore region 27 is larger than the bore region 23 and, unlike the bore region 23, is large enough to pass the enlargement 17.

Coated onto the surface 29 of the shroud 19 which faces in substantially the same direction as the tip 13 of the needle 11 is a layer of an adhesive 31. The adhesive 31 is one that can removably affix to the skin such as a tacky cement of the type commonly used on surgical tape for bandages. The adhesive 31 is selected and applied over a large enough surface of the shroud 19 so as to adhere to the skin with a force greater than the frictional force between the shroud 19 and the needle 11. The exposed face of the adhesive may be covered with a protective releasable strip (not shown) that can be peeled away and discarded immediately prior to use of the syringe 1.

Referring now specifically to FIG. 1, the syringe 1 is shown with the needle 11 fully inserted into the skin 15 of a living being. In this disposition, the shroud 19 is in a first position adjacent the frustoconical end 5 of the syringe reservoir 3 with its surface 29 fixed by the adhesive 31 to the skin 15. As can be seen in FIG. 2, there is sufficient extension of the needle 11 beyond the shroud 19 to permit sufficient penetration of the needle tip 13 into the skin 15 for an injection or withdrawal of body fluid.

Although FIG. 2 shows the needle in a position transverse to the surface of the skin as is often the practice when a serum is injected into a patient, the needle may penetrate at an angle oblique to the skin surface, as is frequently the practice when blood is drawn or a fluid is administered intravenously. It is only necessary that the surface of the shroud which will engage the skin when the needle is inserted be provided with the adhesive.

Figure 3:
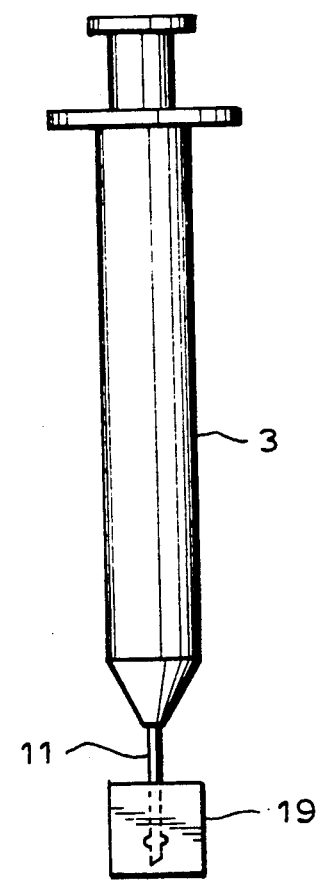
FIG. 3 is an elevation view of the apparatus of the preferred embodiment of the invention in an intermediate disposition.

Upon completion of the injection or withdrawal of body fluid, the syringe 1 with needle 11 is withdrawn from the skin while the shroud 19 remains affixed to the skin, as shown in FIG. 3, until the tip 13 of the needle 11 passes completely through the narrow bore region 27 in the shroud 19 and enters the enlarged bore region 25. Once the tip 13 of the needle 11 enters the enlarged bore region 25 the needle 11 can be readily canted with respect to the shroud 19

As the syringe 1 with needle 11 is withdrawn from the skin 15, enlargement 17 engages the interior wall of the shroud 19 where the enlarged bore region 25 meets the canted narrow bore region 23. Because the bore region 23 is smaller than the enlargement 17 on the needle 11, the enlargement 17 pulls against the shroud 19 as the syringe 1 and needle 11 are further withdrawn thereby breaking the bond between the adhesive 31 and skin 15 and pulling the shroud 19 away from the skin 15.

Once the shroud 11 is free of the skin 15 with the tip 13 of the needle 11 within the enlarged bore region 25, the canted bore region 23 is urged to align with the needle 11 thereby canting the shroud 19 so that the tip 13 of the needle 11 is entrapped within the shroud 19 as shown in FIG. 4. In this position, the needle 11 is safe as its tip 13 is fully covered by the shroud 19 and inaccessible.

It is to be appreciated that the foregoing is a description of a preferred embodiment of the invention to which variations and modifications may be made without departing from the spirit and scope of the invention. For example, instead of the reservoir being contained within a syringe, the reservoir may be an intravenous bottle or bag connected to a needle through flexible tubing. Moreover, no reservoir is necessary as any needle or puncturing device adapted to penetrate the skin, which can thereafter carry infectious organisms, can be protected after use in accordance with the teachings of the invention.

What is claimed is:

1. An improved apparatus for passing a fluid through the skin of a living being, having a reservoir for storing and supplying said fluid and a hollow tubular needle with a reservoir end connected to one end of said reservoir and an opposite penetrating end for penetrating the skin, wherein the improvement comprises a shroud axially slidably mounted on said needle for movement between a first position at which said penetrating end of said needle is exposed and a second position at which said penetrating end of said needle is covered by said shroud, said shroud having a bore therethrough, said needle being slidably received in said bore and in frictional engagement with said shroud at narrowed spaced regions of said shroud respectively proximal to and distal from said reservoir when in said first position, the axis of said bore at said proximal region being out of alignment with the axis of said bore at said distal region so that when said shroud is in said second position the axis of said bore at said distal region is out of alignment with the axis of said needle thereby preventing said shroud from returning to said first position.

2. An improved apparatus according to claim 1 further comprising skin adhesion means on said shroud for releasably securing said shroud to the skin whereby said shroud is urged from said first position to said second position as said needle is withdrawn from the skin.

3. An improved apparatus according to claim 2 wherein said adhesion means comprises a tacky element.

4. An improved apparatus according to claim 1 further comprising limiter means mounted on at least one of said reservoir and said needle and engageable with said shroud at said second position for preventing said shroud from separating from said needle.

5. An improved apparatus according to claim 4 wherein said limiter means comprises an enlargement on said needle intermediate its ends and said shroud bore has a region intermediate said reservoir and said needle enlargement narrower than said enlargement whereat said enlargement is engaged by said shroud for preventing said shroud from sliding beyond said second position.

6. An improved apparatus according to claim 1 wherein said reservoir comprises a syringe.

7. A method of protecting against inadvertent puncture by a needle after it has penetrated and been withdrawn from the skin of a living being comprising
axially slidably mounting a shroud on said needle for movement between a first position at which said penetrating end of said needle is exposed and a second position at which said penetrating end of said needle is covered by said shroud, and
supporting said shroud on said needle when in said first position at misaligned bore portions respectively proximal to and distal from said reservoir for forcing said shroud distal bore portion out of alignment with said needle when said shroud is in said second position.

8. A method of protecting against inadvertent puncture by a used needle according to claim 7 further comprising limiting movement of said shroud with respect to said needle to prevent said shroud from separating from said needle after said needle tip is covered by said shroud.

9. A method of protecting against inadvertent puncture by a used needle according to claim 7 further comprising adhering said shroud to the skin before said needle is withdrawn therefrom whereby said shroud is slid over the tip of said needle as it is withdrawn.

* * * * *